(12) United States Patent
Barrett et al.

(10) Patent No.: US 10,430,942 B2
(45) Date of Patent: Oct. 1, 2019

(54) IMAGE ANALYSIS FOR PREDICTING BODY WEIGHT IN HUMANS

(71) Applicant: UNIVERSITY OF KENTUCKY RESEARCH FOUNDATION, Lexington, KY (US)

(72) Inventors: Jeffrey S. Barrett, North Wales, PA (US); Chee Ng, Princeton Junction, NJ (US)

(73) Assignee: University of Kentucky Research Foundation, Lexington, KY (US)

( * ) Notice: Subject to any disclaimer, the term of this patent is extended or adjusted under 35 U.S.C. 154(b) by 327 days.

(21) Appl. No.: 15/026,723

(22) PCT Filed: Oct. 1, 2014

(86) PCT No.: PCT/US2014/058530
§ 371 (c)(1),
(2) Date: Apr. 1, 2016

(87) PCT Pub. No.: WO2015/050929
PCT Pub. Date: Apr. 9, 2015

(65) Prior Publication Data
US 2016/0253798 A1 Sep. 1, 2016

Related U.S. Application Data

(60) Provisional application No. 61/885,222, filed on Oct. 1, 2013.

(51) Int. Cl.
*A61B 5/00* (2006.01)
*G06T 7/00* (2017.01)
(Continued)

(52) U.S. Cl.
CPC .......... *G06T 7/0012* (2013.01); *A61B 5/0062* (2013.01); *A61B 5/0077* (2013.01);
(Continued)

(58) Field of Classification Search
CPC ........................... A01K 11/008; G06T 7/0012
(Continued)

(56) References Cited

U.S. PATENT DOCUMENTS

| | | | |
|---|---|---|---|
| 2003/0108851 A1 | 6/2003 | Posa | |
| 2009/0306484 A1 | 12/2009 | Kurtz et al. | |
| 2010/0312143 A1 | 12/2010 | Kim | |
| 2016/0125276 A1* | 5/2016 | Spicola, Sr. | A01K 11/008 382/110 |

FOREIGN PATENT DOCUMENTS

WO  WO 2012/079014  6/2012

OTHER PUBLICATIONS

We, "A computational approach to body mass index prediction from face images", Apr. 2, 2013.*
(Continued)

*Primary Examiner* — Albert Kir
(74) *Attorney, Agent, or Firm* — Stites & Harbison PLLC; Mandy Wilson Decker; Summer E. Young (57) ABSTRACT

Systems and methods for determining body weight predictions and human conditions are disclosed. A body weight may be predicted by capturing at least one image of a human, and determining, from the image, a body weight prediction of the human by processing the at least one image with a data processor. The body weight prediction may further be based on an age-based weight factor. A model such as a neural network model may be used to predict body weight.

5 Claims, 8 Drawing Sheets

(51) Int. Cl.
    *A61B 5/107*           (2006.01)
    *G06K 9/00*            (2006.01)
    *G06K 9/66*            (2006.01)
    *G06T 11/60*           (2006.01)
    *G16H 50/20*          (2018.01)
    *G06F 19/00*          (2018.01)

(52) U.S. Cl.
    CPC .......... *A61B 5/0082* (2013.01); *A61B 5/1072* (2013.01); *A61B 5/7275* (2013.01); *G06F 19/00* (2013.01); *G06K 9/00281* (2013.01); *G06K 9/66* (2013.01); *G06T 11/60* (2013.01); *G16H 50/20* (2018.01); *A61B 5/7267* (2013.01); *G06K 2009/00322* (2013.01); *G06T 2207/30004* (2013.01)

(58) Field of Classification Search
    USPC .......................................... 348/77; 382/110
    See application file for complete search history.

(56) References Cited

OTHER PUBLICATIONS

Siege, "The relationship between body weight, facial, and dental dimensions in a population of olive baboons (*Papio cynocephalus anubis*)", 1980.*

International Search Report and Written Opinion for PCT/US2014/058530 dated Dec. 29, 2014.

* cited by examiner

Input/output:
  $A_1$: CDC-inferred body weight
  $A_2$: distance"CD"
  $A_3$: distance"FG"
  $A_4$: distance"DE"
  BW: ANN predicted body weight

Model coefficients:

$$X_{offset} = \begin{bmatrix} 20.54 \\ 0.12 \\ 1.74 \\ 0.32 \end{bmatrix} \quad X_{gain} = \begin{bmatrix} 0.04 \\ 10.60 \\ 3.02 \\ 10.32 \end{bmatrix} \quad X_{min} = -1$$

Pre-processing:
  minmax: normalize the input parameters to a rage between -1 and 1
  $x = (A - X_{offset}) \circ X_{gain} + X_{min}$ $$IW = \begin{bmatrix} 0.88 & -2.07 & 2.16 & -5.03 \\ -0.96 & 1.88 & -0.13 & 0.21 \\ 4.26 & -7.51 & 1.36 & 2.08 \\ 0.89 & -4.60 & 0.02 & -0.20 \end{bmatrix} \quad b_1 = \begin{bmatrix} -5.24 \\ -0.20 \\ -1.97 \\ 1.34 \end{bmatrix}$$

Neural network:
  tansig: tan-sigmoid transfer function
  $h_i = \tanh(IW_i * x + b_{1,i})$
  purelin: linear transfer function
  $y = LW * h + b_2$ $$LW = \begin{bmatrix} 1.30 & 1.80 & 0.59 & 1.00 \end{bmatrix} \quad b_2 = 0.93$$

Post-processing:
  $minmax^{-1}$: reversed minmax to scale the output from [-1, 1] to the desired range
  $BW = (y - y_{min})/y_{gain} + y_{offset}$ $y_{min} = -1 \qquad y_{gain} = 0.026 \qquad y_{offset} = 18.6$

FIG. 9b

IMAGE ANALYSIS FOR PREDICTING BODY WEIGHT IN HUMANS

CROSS REFERENCE TO RELATED APPLICATION

This application claims priority to U.S. Provisional application Ser. No. 61/885,222 entitled IMAGE ANALYSIS FOR PREDICTING BODY WEIGHT IN HUMANS, filed on Oct. 1, 2013, which is incorporated fully herein by reference.

FIELD OF THE INVENTION

The present invention relates to predicting body weight.

BACKGROUND OF THE INVENTION

Body weight (BW) is an important physiologic parameters in pediatric medicine given it's an essential factor for determining optimal drug dosages and intravenous fluid requirement, DC shock energy voltage needed for cardiorespiratory arrest, and correct equipment sizes in pediatric patients undergoing resuscitation. For example, many medications for children, including life-saving medications, are dosed on a per weight basis (e.g., mL/kg). Emergency situations, however, may preclude the ability to weigh a child on a scale. In addition, the availability of accurate weight scales is limited in many locations in the developing world. There is a need for methods, systems, and apparatus to accurately and efficiently predict BW without the use of a scale.

SUMMARY OF THE INVENTION

The inventors have recognized that the body weight prediction of a human and the condition of a human can be determined through image analysis. Aspects of the invention are embodied in methods and system for predicting the body weight of a human. Body weigh may be predicted by capturing an image of a face of a subject human, receiving an age factor of the subject human, determining a weight factor for the received age factor from an age-based weight prediction model, determining at least two facial feature measurement factors for the face from the captured image, the at least two facial feature measurement factors including a first facial feature measurement factor extending in a first direction and a second facial feature measurement factor extending in a second direction different from the first direction, and applying the weight factor and the at least two facial feature measurement factors to a trained neural network model to predict the weight of the subject human, the trained neural network model trained with parameters corresponding to the at least two facial feature measurement factors and the weight factor obtained from each of a plurality of other humans.

Further aspects of the invention are embodied in systems for predicting the body weight of a human from at least one image of the human. The system includes a database configured to receive and store a plurality of other human images and configured to receive and store a plurality of body weights associated with the plurality of other human images. The system also includes a data processor coupled to the database configured to receive at least one image of the human from an image source and determine by comparative analysis of the stored plurality of other human images and the stored plurality of body weights associated with the plurality of other human images in the database and the at least one received image, a body weight prediction of the human.

Other aspects of the invention are embodied in methods and systems for determining a condition of a human based on a phenotypic response of the human from at least one image of the human. The systems and methods include a database configured to receive and store a plurality of other human images and configured to receive and store a plurality of phenotypic response data associated with the plurality of other human images. The systems further include a data processor coupled to the database, configured to receive the at least one image of the human from an image source and determine by comparative analysis of the stored plurality of other human images and the stored plurality of phenotypic response data associated with the plurality of other human images in the database and the at least one received image, the condition of the human.

BRIEF DESCRIPTION OF THE DRAWINGS

The invention is best understood from the following detailed description when read in connection with the accompanying drawings, with like elements having the same reference numerals. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Figure 1A:
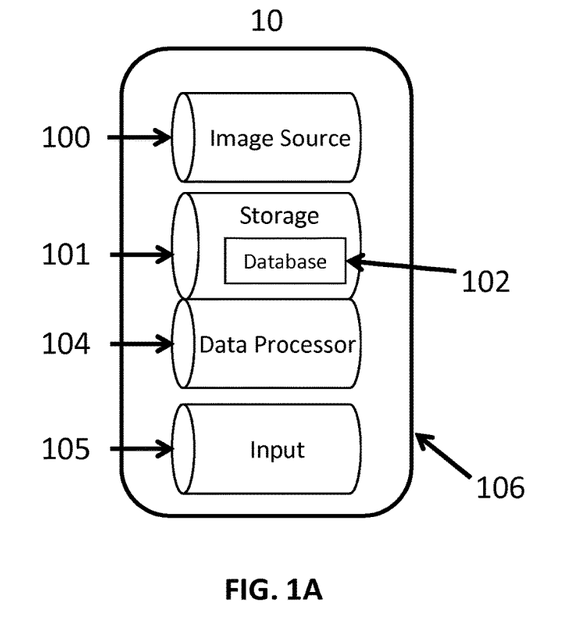
FIGS. 1A, 1B, 2A, and 2B are diagrams of systems for predicting body weight(s) in accordance with aspects of the invention.
Figure 1B:
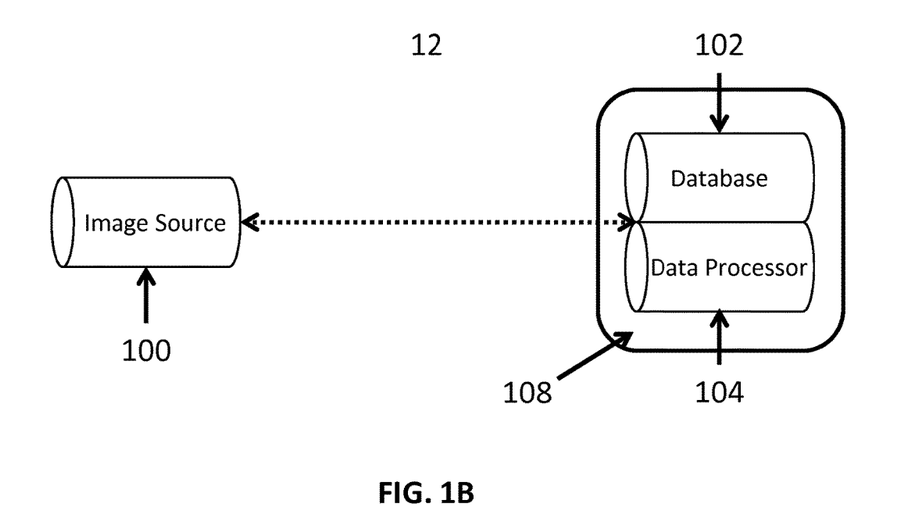

FIGS. 1A and 1B are respective diagrams of body weight (BW) prediction systems 10, 12 in accordance with aspects of the invention for predicting a body weight of a human from at least one image of the human. The systems 10, 12 may also be used to capture, store and decompose anatomic features into quantitative metrics. In an embodiment, systems 10, 12 may be used to determine a body weight prediction for a child from at least one image of the child. As used herein, "child" refers to a human less than eighteen years of age. The predictions may be used to determine other weight related parameters such as body mass index (BMI).

System 10 depicts a device 106 including an image source 100, a storage device 101 including a database 102, a data input 105, and a data processor 104. The device 106 may be a camera, smart phone, tablet device, computer, etc. Other suitable devices will be understood by one of skill in the art from the description herein. In system 12, a remote data processing system 108 is separate from the image source 100. The remote data processing system 108 includes a database 102 and a data processor 104. The remote data processing system 108 may be configured to transmit data to and receive data from the image source 100, another device (e.g., associated with a user), etc. Other suitable system configurations will be understood by one of skill in the art from the description herein.

The image source 100 may be used to capture at least one image (e.g., a digital image) of a human (e.g., an image of a human face). The image source 100 may be a camera, video recorder, computer, smart phone, tablet, etc. The image(s) may be full body images and/or facial images and may include front, profile, and/or back views. Other suitable types of image sources, images and profiles for use in systems 10, 12 will be understood by one of skill in the art from the description herein.

The storage component 101 is configured to store data, e.g., in the database 102. The storage component may be conventional memory. The storage component 101 may store images, data related to images, and/or a model such as a neural network model for processing images/image data.

The database 102 is configured to receive and store a plurality of human images. In one embodiment, the database 102 is further configured to receive and store a plurality of human body weights associated with the plurality of human images. In some embodiments, the database 102 is further configured to store one or more additional pieces of information such as data derived from the Center for Disease Control (CDC) weight-for-age growth curve and/or measurements/statistics derived from the images. As used herein, the terms "body weight" and "body weights" may be used to refer to both actual body weight(s) and predicted body weight(s). The database 102 may be configured to receive and store the at least one captured image from the image source 100. In one embodiment, the database 102 is configured to receive and store the body weight associated with the captured image(s) from the data processor 104. The database 102 may further be configured to store a plurality of phenotypic response data associated with the plurality of human images. Phenotypic response data may include the condition of a human (e.g., fever, bacterial or viral infection, GI-related disturbances, depression, dementia-related central nervous system disorders, etc.) at the time the image is captured.

The data input 105 is configured to receive data that is captured manually and/or automatically. In one example, the data input is a manual data entry device such as a touch screen that a user may use to enter, for example, an age factor, which may be the patient's actual age, an approximation, or a guess. In another embodiment, the data input may be an input from another device such as an age detection application that assesses the patient's age from, for example, an image.

A data processor 104 is coupled to the storage component 101. In an embodiment, the data processor 104 is configured to determine a body weight prediction of a human by comparative analysis of the stored plurality of human images (and/or measurements/statistics derived therefrom) and the stored plurality of body weights associated with the plurality of human images in the database 102 and the at least one captured image of the human (and/or measurements/statistics derived therefrom). In such embodiments, the data processor 104 may be configured to send the at least one captured image (and/or measurements/statistics derived therefrom) and the determined body weight associated with the at least one captured image (and/or measurements/statistics derived therefrom) to the database 102 to store and utilize in future body weight determinations.

The data processor 104 may comparatively analyze the plurality of human images with the captured image by comparing feature points of the images (e.g., age, height, distance between inner ears, head height, distance between eye midpoint and chin, distance between eyes, etc.). Other feature points suitable for comparative analysis in accordance with aspects of the invention will be understood by one of skill in the art from the description herein. The comparative analysis used to determine the body weight prediction may further be based on the patient's age and other data such as the CDC weight-for-age growth curve. The data processor 104 may utilize a model such as a neural network model trained using features for other human beings (and one or more other factors such as CDC weight-for-age charts) in order to determine a predicted weight of a subject human being.

In one embodiment, the data processor 104 is configured to develop a phenotypic response based on a human image. A phenotypic response is an assessment of how the human is feeling and may be linked to certain diseases. The data processor 104 may comparatively analyze the plurality of human images associated with phenotypic response data and the captured image by comparing phenotypic points of the images (e.g., age, facial discoloration, pupil dilation, mouth height and width, eyebrow height, etc.) to determine the condition of the human. Other suitable phenotypic points for determining a phenotypic response will be understood by one of skill in the art from the description herein.

The data processor 104 may be further configured to send the determined body weight prediction and/or phenotypic response to the image source 100 (e.g., a device housing the image source 100), the device 106, another device (e.g., associated with a user), etc. In an embodiment, the data processor 104 is configured to send a medication dose prediction based on the determined body weight prediction to the image source 100 (e.g., a device housing the image source 100), the device 106, another device (e.g., associated with a user), etc., by querying a drug database for weight-based dosing formulas.

The systems 10, 12 of FIGS. 1A and 1B are meant to be exemplary and not exclusive. One of skill in the art will recognize that other system configurations may be used in accordance with aspects of the present invention for determining body weight predictions.

Figure 2A:
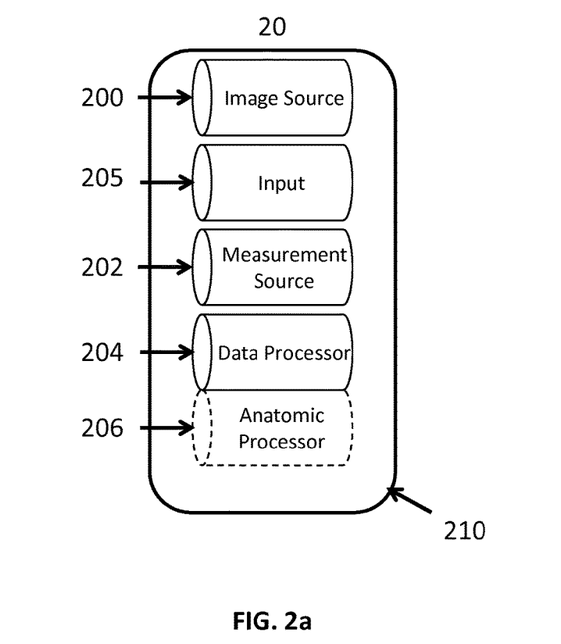
Figure 2B:
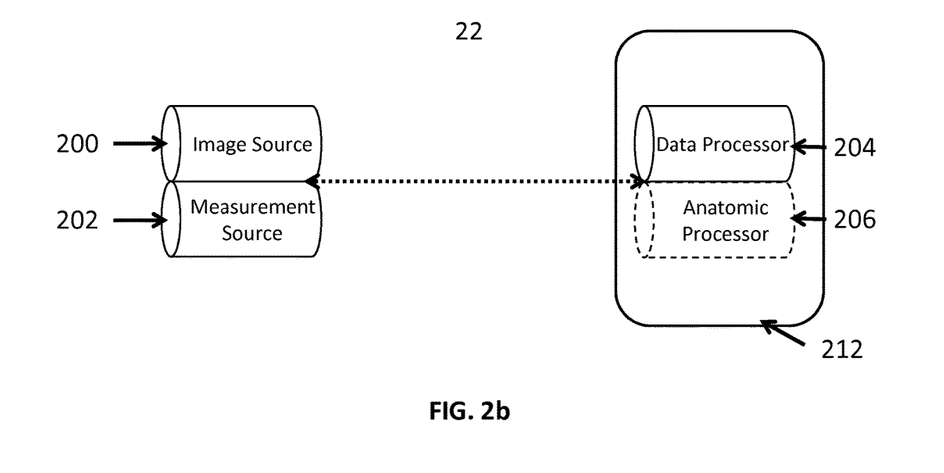

FIGS. 2A and 2B are respective diagrams of body weight prediction systems 20, 22 in accordance with aspects of the invention for predicting a body weight of a human from at least one image of the human and at least one anatomic measurement of the human. The systems 20, 22 may also be used to capture, store and decompose anatomic features into quantitative metrics. In an embodiment, systems 20, 22 may be used to determine a body weight prediction for a child from at least one image of the child and at least one anatomic measurement of the child.

System 20 depicts a device 210 including an image source 200, a measurement source 202, and a data processor 204. The device 210 may be a camera, smart phone, tablet device, computer, etc. Other suitable devices will be understood by one of skill in the art from the description herein. The system 20 optionally includes an anatomic processor 206 incorporated into the device 210. In system 22, a remote data processing system 212 is separate from the image source 200 and the measurement source 202. The remote data processing system 212 includes a data processor 204. The remote data processing system 212 optionally includes an anatomic processor 206. Other suitable system configurations will be understood by one of skill in the art from the description herein.

The image source 200 may be used to capture at least one image (e.g., a digital image) of a human. The image source 200 may be a camera, video recorder, computer, smart phone, tablet, etc. The image(s) may be full body images and/or facial images and may include front, profile, and/or back views. Other suitable types of image sources, images and profiles for use in systems 20, 22 will be understood by one of skill in the art from the description herein.

Figure 4A:
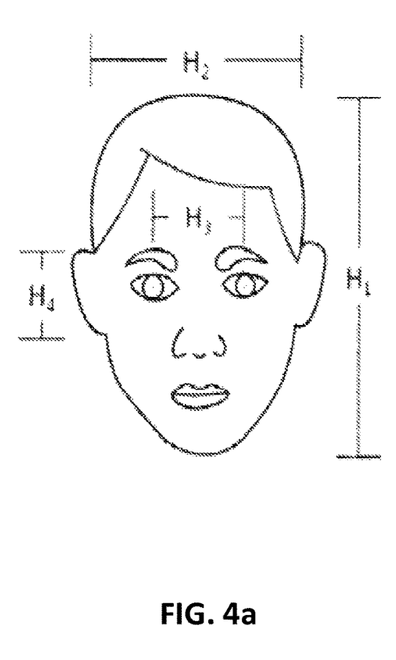
FIGS. 4a and 4b are two front views and FIG. 5 is a profile view of a human face depicting various measurements that may be used to predict body weight(s) in accordance with various aspects of the invention.
Figure 4B:
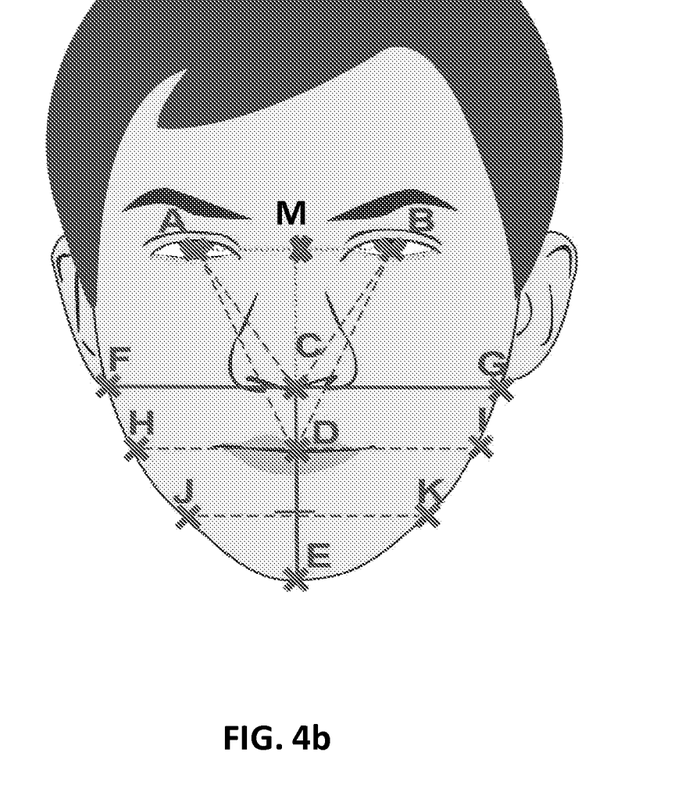
Figure 5:
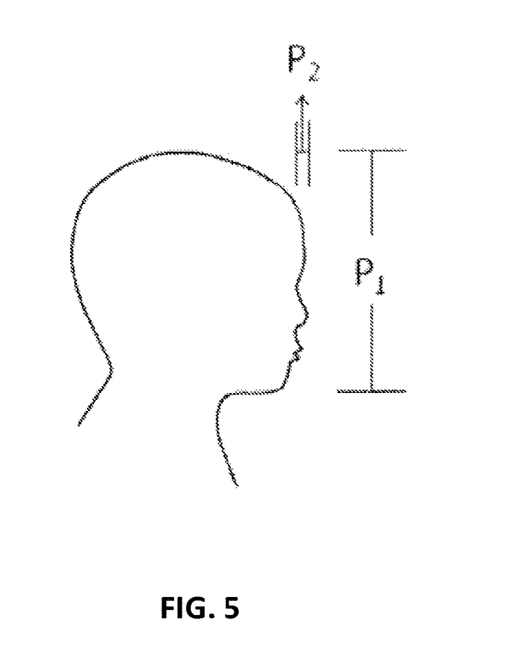
Figure 6:
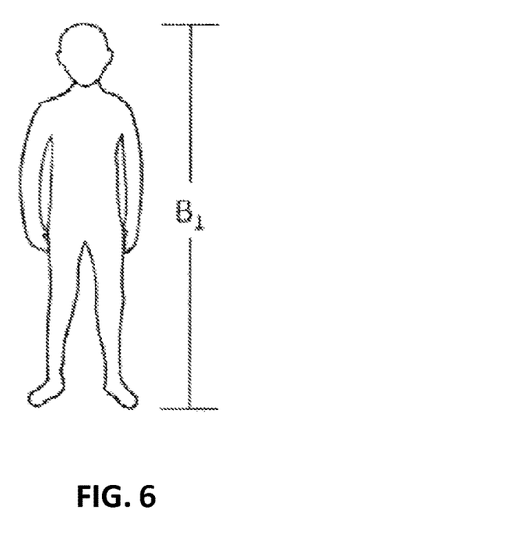
FIG. 6 is a full body view of a human depicting a measurement that may be used to predict body weight(s) in accordance with various aspects of the invention.

The measurement source 202 is configured to receive at least one measured dimension of a human and to send the at least one measured dimension to the data processor 204, the anatomic processor 206, and/or the remote data processing system 212. The at least one measured dimension may be one or more of the dimensions H1, H2, H3, H4 as depicted in FIG. 4a, one or more of the dimensions AB, AC, AD, AM, BC, BD, BM, MC, CD, CE, DE, MD, ME, FC, CG, FG, HD, DI, HI, JK as depicted in FIG. 4b (where A corresponds to a right eye, B corresponds to a left eye, C corresponds to a nose, D corresponds to lips, E corresponds to a chin, F corresponds to a right edge of the face in-line with the nose, G corresponds to a left edge of the face in-line with the nose, H corresponds to a right edge of the face in-line with the lips, I corresponds to a left edge of the face in-line with the lips, J corresponds to a right edge of the face in-line with a midpoint between the lips and the chin, K corresponds to a left edge of the face in-line with a midpoint between the lips and the chin, and M corresponds to a midpoint between the eyes), one or more of the dimensions P1, P2 as depicted in FIG. 5, one or more of the dimension B1 as depicted in FIG. 6, etc. Alternatively, one or more of the dimensions may be derived from the images. The measurement source 202 may also be configured to receive the age of a human and send the age to the data processor 204, the anatomic processor 206, and/or the remote data processing system 212. In one embodiment, the measurement source 202 is configured to receive and send the ethnicity of a human. Other suitable dimensions for measurement will be understood by one of skill on the art from the description herein.

The data processor 204 receives the at least one captured image and the at least one measured dimension. In one embodiment, the data processor 204 calculates at least one anatomic measurement of the human based on the at least one captured image and the at least one measured dimension. The at least one calculated anatomic measurement may be arm circumference, neck, height, limb length, distance between eyes, distance between eye midpoint and nose/lips/chin, etc. Other suitable anatomic measurements to be calculated will be understood by one of skill in the art from the description herein. In an embodiment, the data processor 204 is configured to send the at least one calculated anatomic measurement to the image source 200 (e.g., a device housing the image source 200), the device 210, another device (e.g., associated with a user), etc. In another embodiment, the data processor is configured to send the at least one calculated anatomic measurement to the anatomic processor 206. In an embodiment, the data processor 204 is configured to send a medication dose prediction based on the determined body weight prediction to the image source 200 (e.g., a device housing the image source 200), the device 210, another device (e.g., associated with a user), etc., by querying a drug database for weight-based dosing formulas.

Systems 20, 22 optionally include an anatomic processor 206 configured to determine a body weight prediction of a human based on the at least one calculated anatomic measurement. In one embodiment, the anatomic processor 206 determines a body weight prediction of the human using the at least one calculated anatomic measurement and a known body weight prediction model (e.g., CDC weight-for-age, Mercy tape, APLS, ARC, Argall formula, Broselow, Cattermole, Leffler, Luscombe & Owens, Nelson, Shann, Theron, Traub-Johnson, Traub-Kichen, etc.). In an embodiment, the anatomic processor 206 determines a body weight prediction of the human using a regression model based on feature point measurements calculated from the image (i.e. height, width of head, distance between eye midpoint, head height, etc.) Other suitable feature point measurements to be calculated from the image will be understood by one of skill in the art from the description herein. The data processor 204 may be configured to perform the processing function of the anatomic processor 206.

The systems 20, 22 of FIGS. 2A and 2B are meant to be exemplary and not exclusive. One of skill in the art will recognize that other system configurations may be used in accordance with aspects of the present invention for determining body weights.

Figure 3:
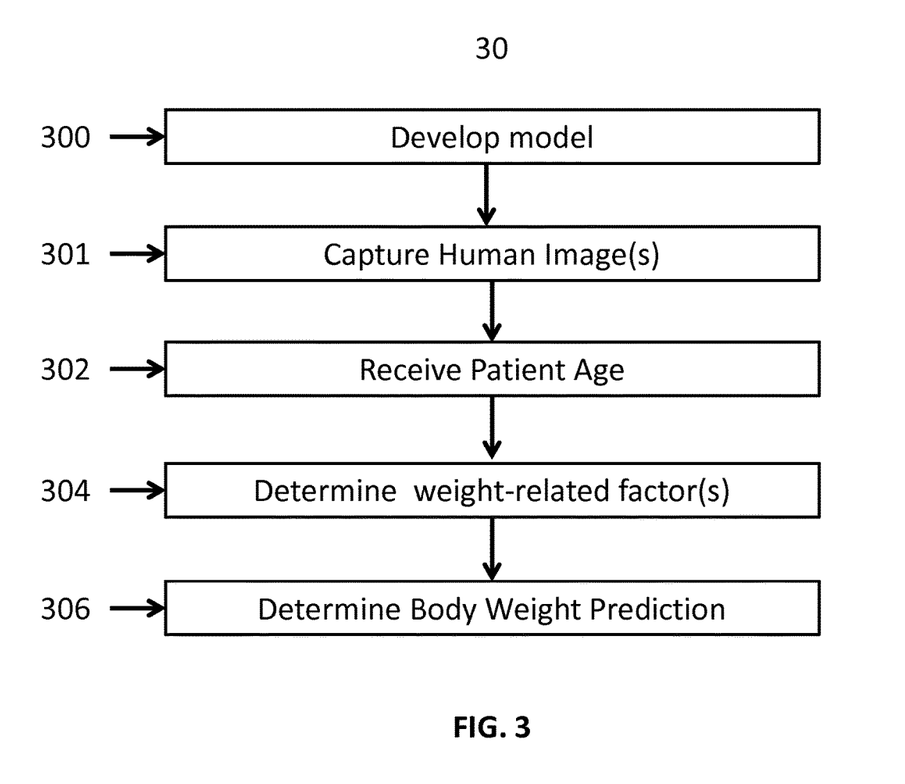
FIG. 3 is a flowchart of exemplary steps for predicting body weight(s) in accordance with aspects of the invention.

FIG. 3 is a flowchart 30 of steps of a method for predicting the body weight of a subject human (e.g., patient). At block 300, a model is optionally developed. The model may be a neural network model. At block 301, at least one image of the subject human is captured. The image(s) may be captured by an image source, e.g., of a camera, smart phone, tablet device, computer, etc. In an embodiment, the subject human is a child. The image(s) may be full body images and/or facial images and may include front, profile, and/or back views. Other suitable types of image sources, images and profiles will be understood by one of skill in the art from the description herein.

At block 302, an age factor for the patient age may optionally be received by a data processor. The age factor may be received via a conventional user input device associated with the devices 106/210 (e.g., a touch sensitive display screen). Alternatively, the age factor may be determined automatically, e.g., from an image using an image processor. The data processor may also receive additional data of the human (e.g., ethnicity, etc.).

At block 304, at least one weight-related factor is determined. As used herein, the term "weight-related factor" refers to a dimension (e.g., length, width, weight) that may be used in predicting body weight. The weight-related factor(s) may include weight factors and/or measurement factors. The factor(s) may be determined, for example, via manual measurement and input via a data input 205 and/or automatically, e.g., by data processor 104/204 from images received from an image source, devices 106 and/or 210, another device (e.g., associated with a user), etc.

The weight-related factor(s) may be a dimension such as at least one of H1, H2, H3, H4 as depicted in FIG. 4a, at least one of AB, AC, AD, AM, BC, BD, BM, MC, CD, CE, DE, MD, ME, FC, CG, FG, HD, DI, HI, JK as depicted in FIG. 4b, at least one of P1, P2 as depicted in FIG. 5, at least one of B1 as depicted in FIG. 6, etc. Other suitable factors for measurements will be understood by one of skill in the art from the description herein. The weight-related factor(s) may also include a dimension such as a weight factor based on a weight prediction model, for example, an age-based weight prediction model based on the received age factor. The weight prediction model may be, for example, CDC weight-for-age, Mercy tape, APLS, ARC, Argall formula, Broselow, Cattermole, Leffler, Luscombe & Owens, Nelson, Shann, Theron, Traub-Johnson, Traub-Kichen, etc.

In an embodiment, the weight-related factors may include at least two facial feature measurement parameters and at least one weight factor. The at least two facial feature measurement factors may include including a first facial feature measurement factor extending in a first direction (e.g., horizontal) and a second facial feature measurement factor extending in a second direction different from the first direction (vertical). The at least two facial feature parameters may include a third facial feature measurement factors extending in substantially the same directed as the second facial feature measurement parameter. The first facial feature measurement parameter may extend between the edges of the face in-line with the nose (e.g., segment FG in FIG. 4b), the second facial feature measurement factor may extend between the nose and the lips of the face (e.g., segment CD in FIG. 4b), and the third facial feature measurement factor may extends between the lips and the chin of the face (e.g., segment DE in FIG. 4b).

The determination of a weight-related factor may include calculating at least one anatomic measurement based on the at least one captured image at block 300 and the at least one measured dimension. The at least one anatomic measurement may be arm circumference, neck, height, distance between eye midpoint, and/or any other anatomic measurement capable for use in body weight prediction(s) as will be recognized by one of skill in the art. The at least one anatomic measurement may be determined by an image analysis algorithm.

At block 306, the body weight prediction of the human in the at least one captured image is determined. In an embodiment, the body weight prediction of the human is determined based only on factors derived from the face of the human and, optionally, a weight factor determined from a weight prediction model as compared to corresponding factor(s)/weights for other humans. The body weight prediction may be determined from the at least one factor determined at block 304. The body weight prediction may be determined by applying the factors to a model. In an embodiment, the body weight prediction is determined using a regression model based on feature point measurements/factors determined from the image (e.g., height, width of head, distance between eye midpoint, head height, etc.) In another embodiment, the body weight prediction is determined using a neural network model.

Figure 7:
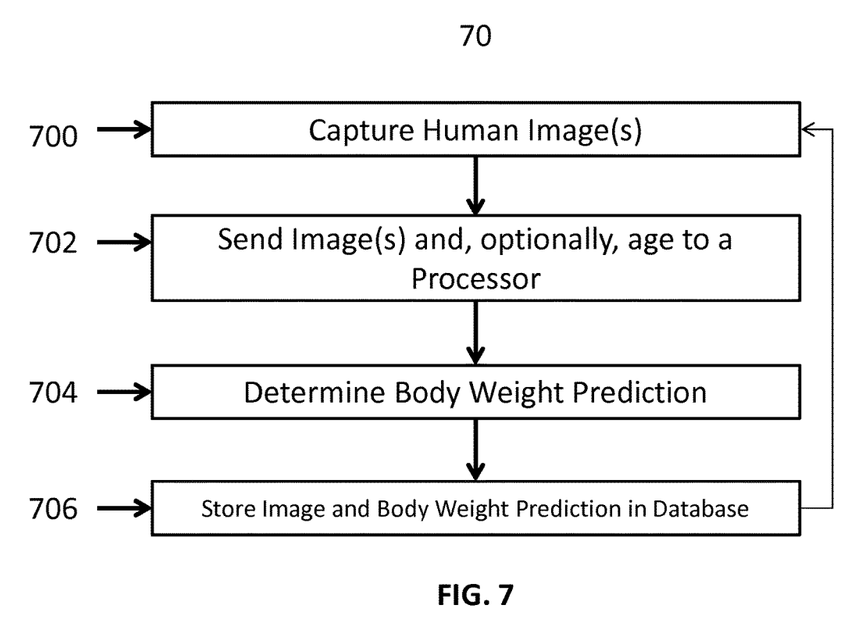
FIG. 7 is another flowchart of steps for predicting body weight(s) in accordance with aspects of the invention.

FIG. 7 is a flowchart 70 of steps of another method for predicting the body weight of a human. At block 700, at least one image of a human is captured. The image(s) may be captured by an image source, e.g., of a camera, smart phone, tablet device, computer, etc. In an embodiment, the human is a child. The image(s) may be full body images and/or facial images and may include front, profile, and/or back views. Other suitable types of images and profiles will be understood by one of skill in the art from the description herein.

At block 702, the at least one captured image is sent to a data processor for analysis. The data processor may be coupled to a database. In one embodiment, the database is configured to receive and store a plurality of human images and receive and store a plurality of body weights associated with the plurality of human images.

At block 704, the data processor determines a body weight prediction of the human in the at least one captured image. In one embodiment, the data processor determines the body weight prediction by comparative analysis of the plurality of human images and plurality of body weights associated with the plurality of images in the database and the at least one image captured at block 700. The data processor may comparatively analyze the plurality of human images with the captured image by comparing feature points of the images (e.g., age, height, distance between inner ears, head height, distance between eye midpoint, etc.). Other feature points suitable for comparative analysis in accordance with aspects of the invention will be understood by one of skill in the art from the description herein.

At block 706, the data processor sends the at least one image captured at block 700 and the body weight prediction determined at block 704 associated with the captured image to the database to be stored. In one embodiment, the determined body weight prediction is transmitted an image source, the device 106 and/or 210, another device (e.g., associated with a user), etc.

It is contemplated that the method of flowchart 70 is not limited to the use of determining body weight predictions. For example, at block 702, the data processor may be configured to receive and store a plurality of phenotypic response data associated with the plurality of human images. Furthermore, at block 704, the data processor may comparatively analyze the plurality of human images associated with phenotypic response data and the captured image by comparing phenotypic points of the images (e.g., age, facial discoloration, pupil dilation, mouth height and width, eyebrow height, etc.) to determine the condition of the human in the captured image. Other suitable phenotypic points for determining a phenotypic response will be understood by one of skill in the art from the description herein. In one embodiment, the data processor at block 706 is configured to send a medication dose prediction based on the determined body weight prediction to the image source, the device 106 and/or 210, another device (e.g., associated with a user), etc., by querying a drug database for weight-based dosing formulas.

In one example, a model for predicting body weight (BW) was developed using data collected from thirty-nine volunteer subjects that included their height, weight, age, gender (25 male, 14 female) and race/ethnicity (28 Caucasian, 1 African American and 9 Asian), as well as full body and facial digital images (frontal and profile). Demographic partitions for sex (25 male, 14 female) and race (28 Caucasian, 1 African American and 9 Asian) were not based on a priori defined stratification. It will be understood that it may be possible to obtain better results by developing models using more subjects. The model described below is a neural network model.

Digital images were obtained using various image sources such as smartphones (e.g., Android, iPhone, etc) and digital cameras. The mean ages of the subjects was 14.6 (range: 6~18) years, and the mean weight was 53.2 (range:

18.6~96.4) kg. Additionally, the CDC weight-for-age growth curve was integrated into the model to predict BW.

The median curves of the CDC weight-for-age growth charts for male and female with ages between two and twenty years were formulated with a fourth-order polynomial regression using a growth charts percentile data file. The formula was used to calculate the CDC-inferred body weight prediction for each subject based on the age and sex. Facial features of the each subject were labeled and measured manually for this study. It is contemplated that the facial features could be captured automatically. Eleven major facial landmark points were selected, and ten facial feature distances were measured (FIG. 4A). The measurements were scaled and normalized two-dimensionally: horizontal distances were scaled relative to the eye-to-eye distance AB and vertical distances were scaled relative to the length of the face EM, which was calculated from:

$$EM = ED + DC + CM = ED + DC + \sqrt{AC^2 - \left(\frac{AB}{2}\right)^2}$$

After normalization, 7 facial feature distances: CD, DE, HI, FG, JK, (AC+BC)/2, and (AD+BD)/2 were used for the model searching.

Figure 8B:
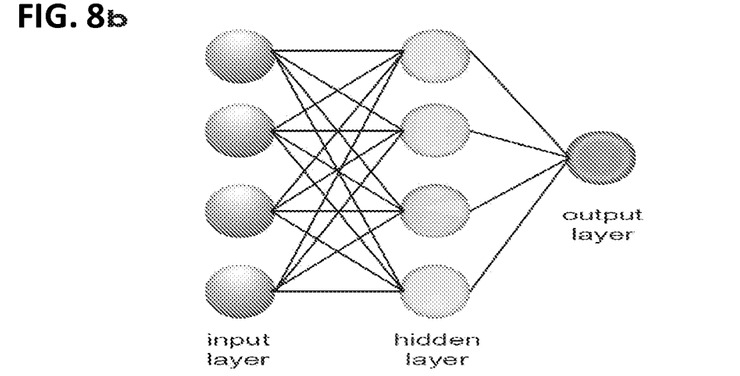
FIG. 8b depicts a schematic of the components of an exemplary neural network model in accordance with aspects of the invention.
Figure 9A:
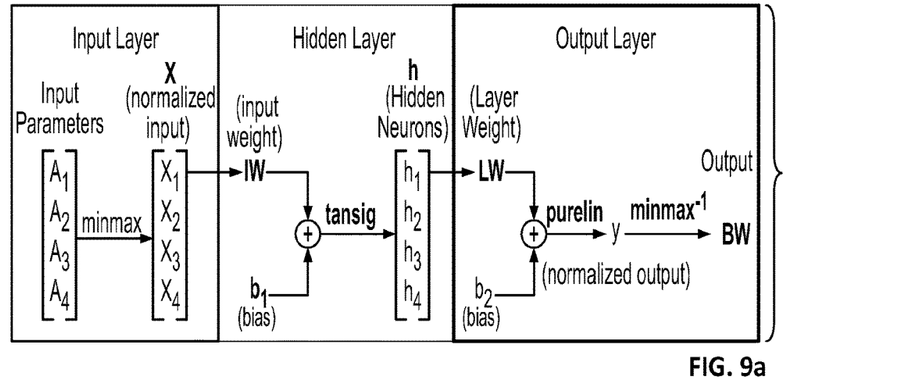
FIG. 9a depicts a schematic of the artificial neural network calculation process in accordance with aspects of the invention.
Figure 9B:
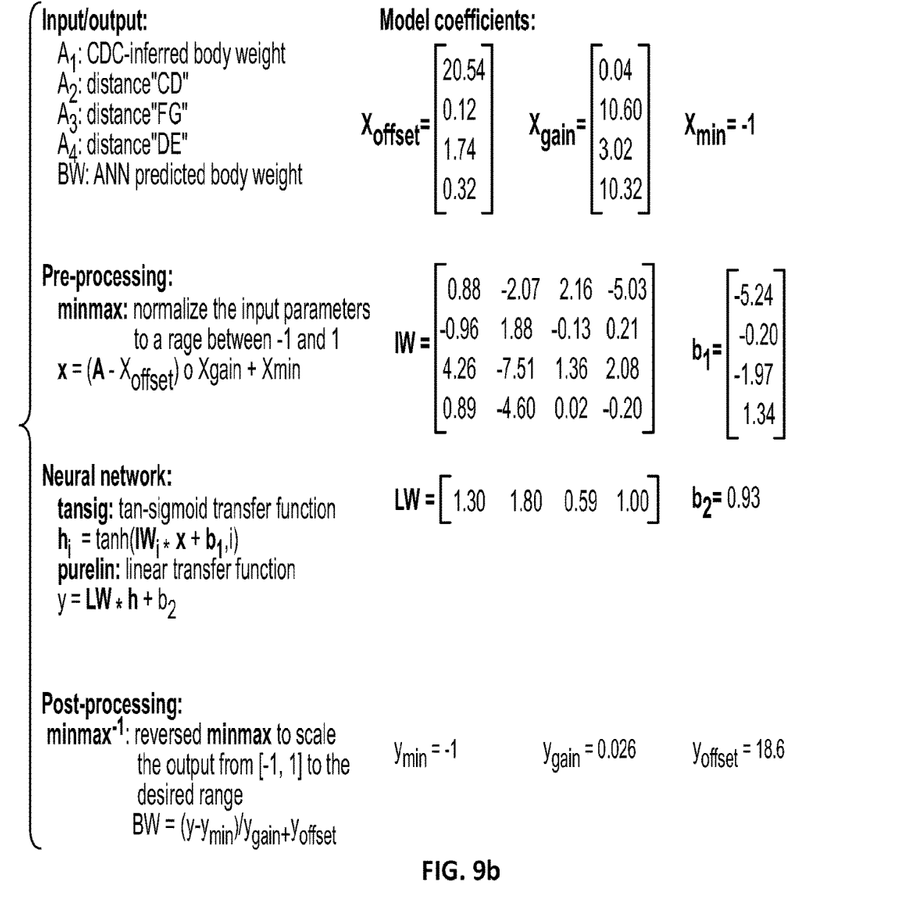
FIG. 9b depicts a mathematical representation of a final neural network model in accordance with aspects of the invention.

Along with the age-based body weight prediction from the median CDC formula, the eight parameters were used as inputs to create the body weight prediction model using a three-layers feed-forward artificial neural network (ANN) using MATLAB and Neural Network Toolbox Release 2014a (The Math Works, Inc., Natick, Mass., USA, http://www.mathworks.com/). ANN is a machine learning method that can be used for non-linear regression. With reference to FIGS. 8b, 9a, and 9b, the ANN training applied tan-sigmoid transfer functions that used the input parameters to calculate a series of intermediate values (hidden neurons), and a linear transfer function that used linear combinations of the hidden neurons to calculate the output. The dataset was randomly divided into a training set (70%), a validation set (15%) and a test set (15%). The training process uses the training set data to continuously adjust weights and biases to improve the training performance of the regression model generated in each repetition (epoch), and the performance of the validation set is calculated for the model at each epoch to verify that no over-fitting occurs. During the training process, if the validation mean squared error (MSE) increases for six consecutive epochs, training is aborted. The last validated model is returned, and then MSE of test set is calculated and recorded. Since the training process randomly assigns initial weights and biases that influence the training results, the process was repeated (retrained) with one thousand iterations, and the model with smallest test set MSE was adopted.

During the model selection process, the ANN models were built with a combination of one to six hidden neurons and one to eight input parameters. The entire eight by six combination space of hidden neuron and input parameters was sampled. For each number of hidden neurons, the starting model has all eight input parameters, and then the input parameters were removed one by one based on the MSE of the same model complexity. For each model, the Akaike Information Criterion (AIC) was calculated using the formula:

$$AIC = -n\log\frac{\sum_{j=1}^{n}(y_j - \hat{y}_j(k))^2}{n} + 2(p+1)$$

where n is the number of samples and p is the overall number of parameters of the ANN. Among the overall models with different number of parameters, the model with smallest AIC was selected as the final optimal model. The bias and precision of the model prediction were assessed using mean prediction error (MPE) and MSE, respectively. In addition, a proportion of the studied population with percent absolute prediction error larger than 5%, 10% and 20% were used to determine the model performance.

Figure 8A:
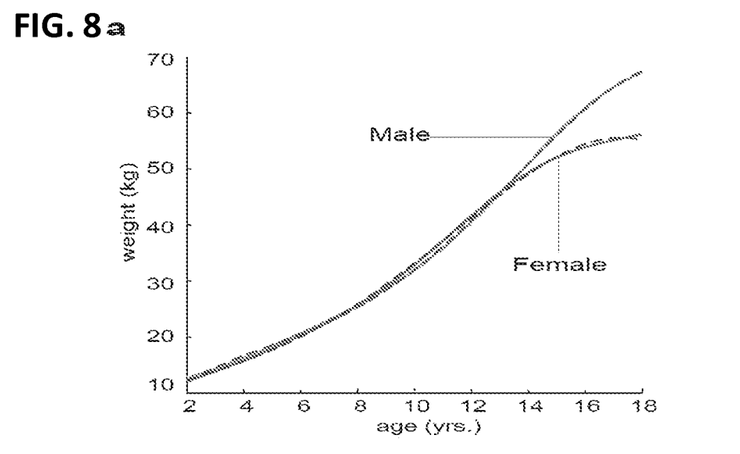
FIG. 8a is a graph depicting CDC weight-for-age median curves reproduced from CDC data (solid) and the fourth order polynomial curve-fitting of each curve (dashed) for use in accordance with aspects of the invention.
Figure 8C:
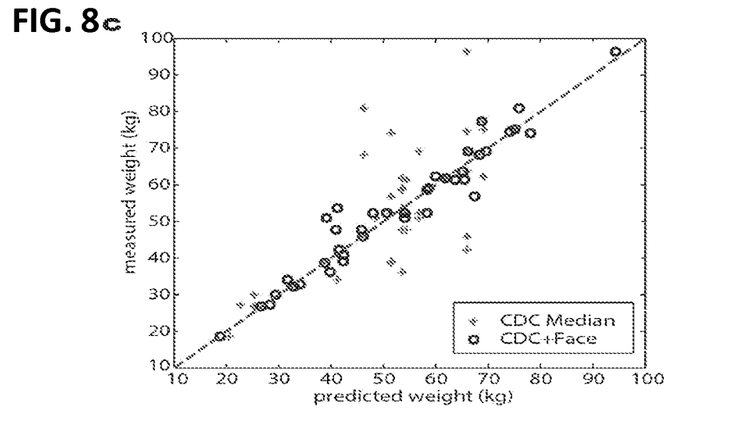
FIG. 8c depicts a graph of measured weight of the subjects vs. weight predicted from the CDC weight-for-age median value (cross) and from the final neural network model (circle) in accordance with aspects of the present invention.

FIG. 8a depicts CDC weight-for-age median curves reproduced from CDC data (solid) and the fourth order polynomial curve-fitting of each curve (dashed). FIG. 8b depicts a schematic of the components of an exemplary neural network model. FIG. 8c depicts measured weight of the subjects vs. weight predicted from the CDC weight-for-age median value (cross) and from the final neural network model (circle).

The CDC median weight-for-age curves are well described by fourth-order polynomial regression, and the R2 of the two curves were both close to 1 (FIG. 8a). The CDC-inferred weight of each subject was calculated based on sex and age, and was used as a control reference to compare the results obtained from the developed model. The body weights were roughly estimated with a fourth-order polynomial regression equation developed using the CDC median weight-for-age curve (R2=0.50, MPE=−1.52 MSE=142.50), but the accuracy for the weight prediction was poor with only 25.6%, 43.6% and 74.4% of the population with relative prediction error within 5%, 10%, and 20%, respectively.

The CDC-inferred weight and the seven measured facial features parameters were used to develop the ANN model. The final model consisted of four parameter inputs (CDC median curve and three facial feature distances: CD, DE, and FG) and four hidden neurons (FIG. 8b). The percent coefficient of variation calculated from the normalized manual measurements by three observers is 5.29%. The schematic of the ANN calculation process and the mathematical representations of the current model are shown in FIGS. 9a and 9b. The selected model has a MPE of 0.48 and MSE of 18.43. Among the predicted values, 64.1% of the predictions fall within 5% error, 84.6% fall within 10% error, and 94.9% fall within 20% error. The coefficient of correlation (R2) value of the prediction of the overall data is 0.94, which is much higher than the value of 0.50 for CDC-inferred body weight (FIG. 8c). With this model, only a total of three normalized facial features distances (CD, DE, and FG in FIG. 4b) derived from seven facial points (Points A-G in FIG. 4b) were needed from the facial digital image to perform weight predictions.

FIG. 4b depicts facial feature measurements for the weight prediction model. The solid lines indicate the measurements used in the final model; the dotted lines are the reference measurements for calibration; and the dashed lines are the lines used during training and were eliminated in the final model.

Weight prediction based only on the CDC curve yields insufficient accuracy to guide individual dosing (R2=0.50, RMSE=12.09). The addition of facial feature measurements to the CDC-predicted BW using a neural network provided a significant improvement in the prediction (R2=0.94, RMSE=3.49)

In accordance with an aspect of the invention, a novel weight prediction method was developed based on age-based CDC-inferred median weight and three unique facial features from digital images. Although age-based CDC median weight alone was a weak predictor of the individual weight in the studied pediatric population, it was a significant parameter during the ANN model development process. Removing age-based CDC median weight prediction from the input in any ANN model would cause a significant decrease in R2 and an increase in prediction error. The MPE and MSE for the best ANN model without age-based CDC median weight were 0.49 and 52.3, respectively. This finding suggests that some age information is useful in order to improve weight prediction closer to the observed weight allowing facial features obtained from digital images to further refine the prediction. After replacing the age-based CDC median weight with age itself, the MPE and MSE for the best ANN model of the same model complexity were −0.048 and 94.4, respectively, which is greater than those observed in ANN model using the age-based CDC median weight, so the age-based CDC median weight prediction is useful for the accuracy of the prediction.

The MPE and MSE for the male subjects are 0.41 and 6.40, respectively, and for female subjects are 0.59 and 39.93, respectively. Although the errors for both sexes are smaller than the error produced by the CDC-inferred weight, the prediction errors for female subjects are higher than the errors for male subjects. A larger sample size is contemplated for determining the prediction bias from sex difference.

Using the CDC curve as the base of the model has the advantage of being able to extrapolate the weight prediction to a population with wider age range. Ethnicity is also correlated with facial features and dimensions as well as weight. However, the final ANN method does not show prediction bias related to ethnicity suggesting that the dependency of the weight and face on ethnicity was accounted for after the weight and selected facial features were included in the model.

The ANN approach was adopted because it is an efficient way to train non-linear regression models using machine learning. Other linear regression methods including bidirectional stepwise regression were used. However, the best linear model trial has a MSE value of 66.01 and 14 parameter terms (including product terms) which has significantly higher error and AIC value than the selected ANN model. Although an ANN model is more complicated than linear regression models, the selected ANN model can be easily saved into and used as a computational function in MATLAB or in other languages. The methodology for body weight prediction based on this approach can be automated with the development of a facial feature extraction algorithm, as selected features are major facial landmarks and there are many different existing robust methods of facial detection and feature extraction that may be useful for this application. For example, facial feature recognition may be accomplished using a face features recognition algorithm that can detect, extract and measure the facial features to predict body weight. Such a face features recognition algorithm can be programmed for use in in iOS and Android-based mobile devices.

The body weight determined in accordance with aspects described herein may be processed, e.g., by data processor 104, to determine other measurements. For example, the body weight of a subject may be combined with the height and/or surface area (obtained through manual measurements and/or through analysis of images) of the subject to determined body mass index using conventional algorithms. Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for predicting body weight of a human subject, the method comprising:
    capturing an image of a face of the subject;
    receiving an age factor of the subject;
    determining a weight factor for the received age factor from an age-based weight prediction model; determining at least three facial feature measurement factors for the face from the captured image, the at least three facial feature measurement factors including a first facial feature measurement factor extending in a first direction, a second facial feature measurement factor extending in a second direction different from the first direction, and a third facial feature measurement factor extending substantially in the same direction as the second facial measurement factor; and applying the weight factor and the at least three facial feature measurement factors to a trained neural network model to predict the weight of the subject human, the trained neural network model trained with parameters corresponding to the at least three facial feature measurement factors and the weight factor obtained from each of a plurality of other human subjects; wherein the face includes a right eye, a left eye, a nose, lips, and a chin, and wherein the facial feature measurement factors include:
    the nose to the lips;
    the lips to the chin;
    a right edge of the face in-line with the lips to a left edge of the face in-line with the lips;
    a right edge of the face in-line with the nose to a left edge of the face in-line with the nose;
    a right edge of the face in-line with a midpoint between the lips and the chin to a left edge of the face in-line with a midpoint between the lips and the chin;
    one half the sum of:
        the right eye to the nose, and
        the left eye to the nose; and
    one half the sum of:
        the right eye to the lips, and
        the left eye to the lips.

2. The method of claim 1 further comprising determining a medication dose, intravenous fluid requirement, or voltage prediction for the subject human based on the determined weight prediction for the human subject.

3. A system for predicting body weight of a human subject, the system comprising:
    a camera to capture images,
    a data input device,
    memory for storing an age-based weight prediction model and a trained neural network model, the trained neural network model trained with parameters corresponding to at least two facial feature measurement factors and a weight factor obtained from each of a plurality of other humans, the at least two facial feature measurement factors including a first facial feature measurement factor extending in a first direction and a second facial feature measurement factor extending in a second direction different from the first direction;

a data processor coupled to the data input device, the camera, and the memory, the data processor configured to capture an image of a face of the human subject with the camera, receive an age factor of the human subject with the data input device; determine the weight factor for the received age factor from the stored age-based weight prediction model; determine the at least two facial feature measurement factors for the face of the human subject from the captured image; and apply the weight factor and the at least two facial feature measurement factors to the trained neural network model to predict the weight of the human subject, further comprising additional facial feature measurement factors, wherein the face includes a right eye, a left eye, a nose, lips, and a chin, and wherein the facial feature measurement factors include:

the nose to the lips;

the lips to the chin;

a right edge of the face in-line with the lips to a left edge of the face in-line with the lips;

a right edge of the face in-line with the nose to a left edge of the face in-line with the nose;

a right edge of the face in-line with a midpoint between the lips and the chin to a left edge of the face in-line with a midpoint between the lips and the chin;

one half the sum of:
  the right eye to the nose, and
  the left eye to the nose; and one half the sum of:
  the right eye to the lips, and
  the left eye to the lips.

4. The system of claim 3, further comprising determining a medication dose, intravenous fluid requirement, or voltage prediction for the subject human based on the determined weight prediction for the human subject.

5. The method of claim 1, further comprising determining a medication dose, intravenous fluid requirement, or voltage prediction for the subject human based on the determined weight prediction for the human subject.

* * * * *